(12) United States Patent
Pearson et al.

(10) Patent No.: US 8,632,534 B2
(45) Date of Patent: Jan. 21, 2014

(54) IRREVERSIBLE ELECTROPORATION (IRE) FOR CONGESTIVE OBSTRUCTIVE PULMONARY DISEASE (COPD)

(75) Inventors: Robert Pearson, San Jose, CA (US); Mark V. Ortiz, San Jose, CA (US); Peter Callas, Castro Valley, CA (US)

(73) Assignee: AngioDynamics, Inc., Latham, NY (US)

( * ) Notice: Subject to any disclaimer, the term of this patent is extended or adjusted under 35 U.S.C. 154(b) by 541 days.

(21) Appl. No.: 12/754,210

(22) Filed: Apr. 5, 2010

(65) Prior Publication Data
US 2010/0256628 A1 Oct. 7, 2010

Related U.S. Application Data

(60) Provisional application No. 61/166,386, filed on Apr. 3, 2009.

(51) Int. Cl.
*A61B 18/18* (2006.01)

(52) U.S. Cl.
USPC .............................................. 606/41; 606/45

(58) Field of Classification Search
USPC ...................................................... 606/32–45
See application file for complete search history.

(56) References Cited

U.S. PATENT DOCUMENTS

| | | | |
|---|---|---|---|
| 4,672,969 A | 6/1987 | Dew | |
| 4,920,978 A | 5/1990 | Colvin | |
| 4,976,709 A | 12/1990 | Sand | |
| 5,122,137 A | 6/1992 | Lennox | |
| 5,281,213 A | 1/1994 | Milder et al. | |
| 5,383,917 A | 1/1995 | Desai et al. | |
| 5,562,720 A | 10/1996 | Stern et al. | |
| 5,586,982 A | 12/1996 | Abela | |
| 5,599,294 A | 2/1997 | Edwards et al. | |
| 5,957,919 A | 9/1999 | Laufer | |
| 6,009,877 A | 1/2000 | Edwards | |
| 6,198,970 B1 | 3/2001 | Freed et al. | |
| 6,280,441 B1 | 8/2001 | Ryan | |
| 6,283,988 B1 | 9/2001 | Laufer et al. | |
| 6,283,989 B1 | 9/2001 | Laufer et al. | |
| 6,299,633 B1 | 10/2001 | Laufer | |
| 6,327,505 B1 | 12/2001 | Medhkour et al. | |
| 6,411,852 B1 | 6/2002 | Danek et al. | |
| 6,488,673 B1 | 12/2002 | Laufer et al. | |
| 6,493,589 B1 | 12/2002 | Medhkour et al. | |
| 6,514,248 B1 | 2/2003 | Eggers et al. | |
| 6,634,363 B1 | 10/2003 | Laufer et al. | |
| 6,989,010 B2 | 1/2006 | Francischelli et al. | |
| 7,027,869 B2 | 4/2006 | Danek et al. | |
| 7,250,048 B2 | 7/2007 | Francischelli et al. | |
| 7,264,002 B2 | 9/2007 | Danek et al. | |
| 7,273,055 B2 | 9/2007 | Danek et al. | |
| 7,655,004 B2 * | 2/2010 | Long ............................ | 606/37 |

(Continued)

FOREIGN PATENT DOCUMENTS

| | | |
|---|---|---|
| WO | 9901076 | 1/1999 |
| WO | 0170114 | 9/2001 |

*Primary Examiner* — Linda Dvorak
*Assistant Examiner* — Amanda Scott
(74) *Attorney, Agent, or Firm* — Ryan D. Artis

(57) ABSTRACT

A method for treating Chronic Obstructive Pulmonary Disease (COPD) or chronic bronchitis to alleviate the discomforts of breathing by using non-thermal electroporation energy to ablate diseased portions of the lung including the bronchus, airways and alveoli which, in effect, opens the restrictive diseased portions thereby maximizing the overall surface area thereof causing improved airflow and uninhibited breathing.

20 Claims, 12 Drawing Sheets

(56) References Cited

U.S. PATENT DOCUMENTS

| | | |
|---|---|---|
| 8,187,269 B2* | 5/2012 | Shadduck et al. ............... 606/41 |
| 2003/0159700 A1 | 8/2003 | Laufer et al. |
| 2003/0212394 A1* | 11/2003 | Pearson et al. ................... 606/41 |
| 2005/0020965 A1 | 1/2005 | Rioux et al. |
| 2006/0247619 A1 | 11/2006 | Kaplan et al. |
| 2008/0015571 A1* | 1/2008 | Rubinsky et al. ............... 606/42 |
| 2008/0097139 A1* | 4/2008 | Clerc et al. ........................ 600/7 |
| 2008/0132826 A1* | 6/2008 | Shadduck et al. ............... 604/24 |
| 2008/0200911 A1* | 8/2008 | Long ............................... 606/34 |
| 2009/0143705 A1 | 6/2009 | Danek et al. |
| 2009/0192508 A1 | 7/2009 | Laufer et al. |
| 2009/0248012 A1* | 10/2009 | Maor et al. ....................... 606/41 |

* cited by examiner

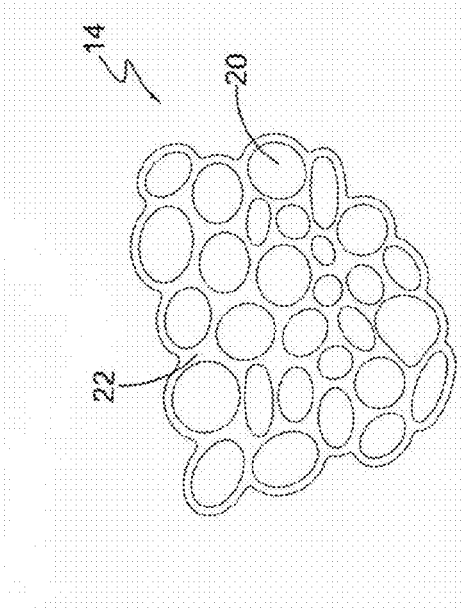
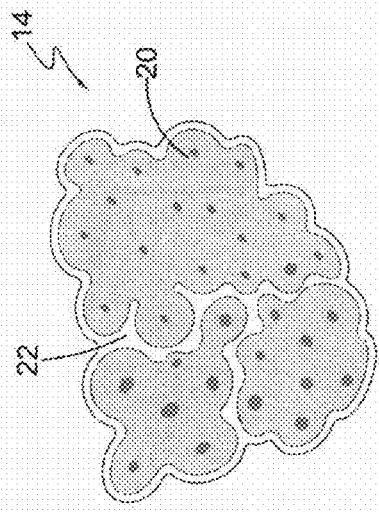

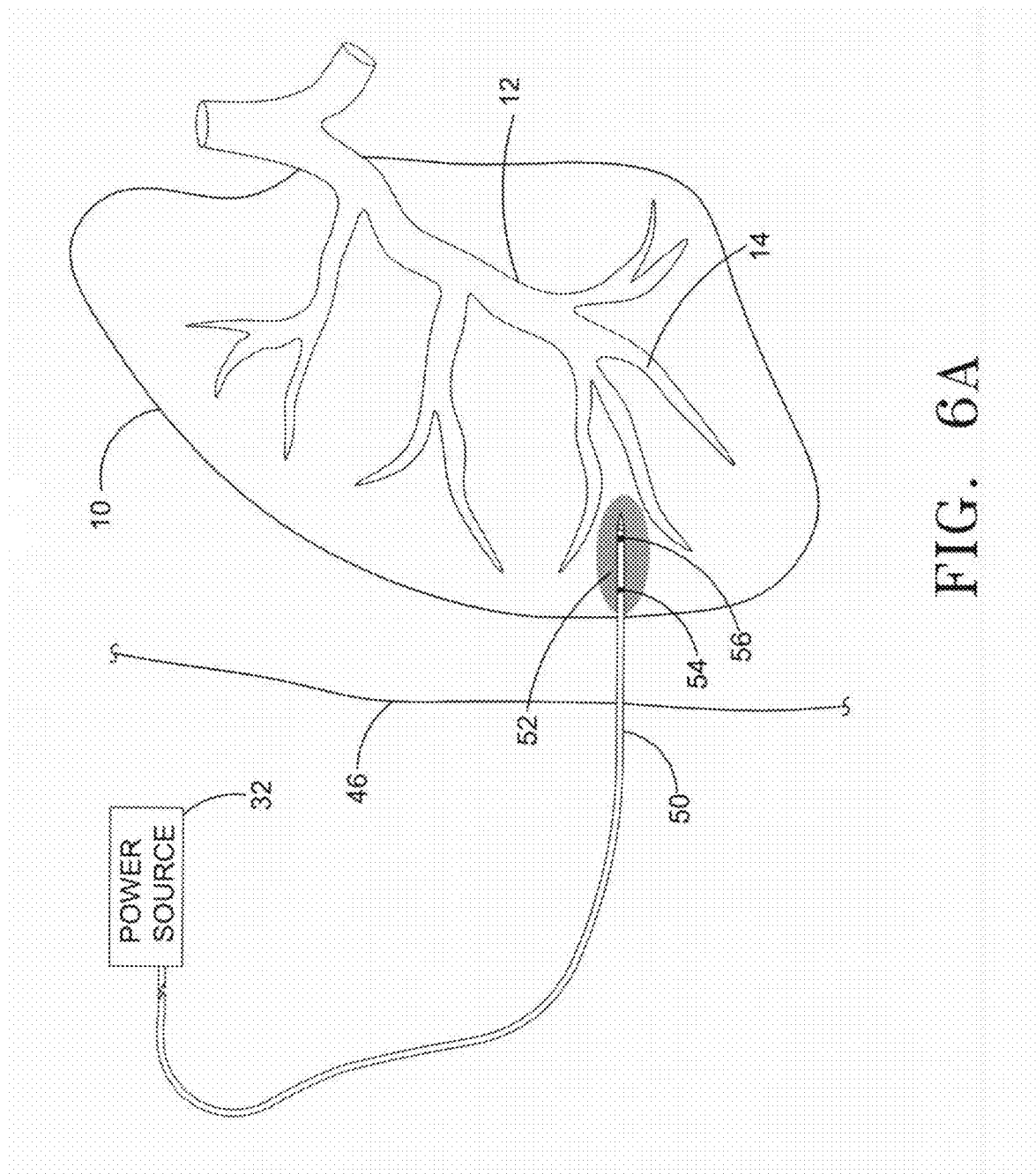

IRREVERSIBLE ELECTROPORATION (IRE) FOR CONGESTIVE OBSTRUCTIVE PULMONARY DISEASE (COPD)

CROSS REFERENCE TO RELATED APPLICATIONS

This application claims priority to U.S. Provisional Application Ser. No. 61/166,386 filed Apr. 3, 2009, which is incorporated herein by reference.

FIELD OF THE INVENTION

The present invention relates to advances in medical procedures aimed at improving the quality and length of life of individuals with Congestive Obstructive Pulmonary Disease (COPD). More particularly, the present invention relates to a method of using Irreversible Electroporation (IRE) to ablate diseased portions of the lung to further enhance lung functions while reducing complications associated with conventional procedures.

BACKGROUND OF THE INVENTION

Chronic Obstructive Pulmonary Disease; hereinafter, COPD is a disease of the lungs wherein the airways become narrowed which leads to a restriction in the flow of air into and out of the lungs causing shortness of breath. COPD includes both chronic emphysema and chronic bronchitis and is mainly caused by noxious particle or gases, most commonly from smoking, which initiates an abnormal inflammatory response in the lung. Other causes of COPD are intense or prolonged exposure to workplace dusts and particles found in coal and gold mining, in the cotton textile industry with chemicals such as cadmium and isocyanates, fumes from welding, and non-smokers being exposed to the noxious particles and gases emitted from smokers. Lung damage, inflammation of the lung airways (alveoli), and clogged mucus in the bronchial tubes are conditions associated with bronchitis and emphysema.

FIG. 1 shows a view of a lung (10) depicting an enlarged bronchus (12) and alveoli (14) which are microscopic grape-like clusters of air sacs at the end of the smallest bronchiole (airways) (12). The alveoli (14) are where gas exchange takes place, and are regarded as the primary functional units of the lungs. Alveoli (14) are densely covered with capillaries [for sake of clarity, too small to show about the alveoli (14), but are extensions to the capillaries (16) about the bronchus (12)] wherein blood is brought to the capillaries (16) by the pulmonary artery (not shown) and carried away by the pulmonary vein (not shown). When the alveoli (14) inflate with inhaled air, oxygen diffuses into the blood in the capillaries (16) to the tissues of the body, and carbon dioxide diffuses out of the blood into the lungs (10), where it is exhaled.

Bronchitis is an inflammation of the bronchial tubes (12), or bronchi, that bring air into the lungs (10). When the cells lining the bronchi are irritated, the tiny hairs (cilia) that normally trap and eliminate particulates from the air stop working. Formation of material (mucus and phlegm) associated with irritation (inflammation) also increases; causing the passages to become clogged. Mucus/phlegm and the inflamed bronchial lining (18 of FIGS. 2A and 2B) constrict the airways causing them to become smaller and tighter which makes it difficult to get air into and out of the lungs. As an attempt to rid the constricted airways of the mucus/phlegm, the body responds with persistent, intense and severe coughing spells. Chronic bronchitis is often either misdiagnosed or neglected until it is in advanced stages.

FIGS. 2A and 2B are cross-sectional views of a normal bronchus (12) and a bronchus (12) affected by chronic bronchitis, respectively. FIG. 2A depicts the bronchus (12) with an inner bronchial wall (18) having a thickness (T1), and the airway (A1) of the bronchus (12) having a diameter (D1). FIG. 2B depicts the bronchus (12) having an inner bronchial wall (18) with a thickness (T2), and the airway (A2) of the bronchus (12) having a diameter (D2). In comparison to a normal bronchus (12), as shown in FIG. 2A, the inner bronchial wall (18) of the bronchus (12) affected by chronic bronchitis has an increased thickness (T2) which creates the decreased diameter (D2) airway (A2). The inner bronchial wall (18) becomes enlarged or swollen due to irritants within the air when air is taken in. Once the inner bronchial wall (18) is irritated, the small hairs (cilia) that normally protect the bronchus (12) from foreign matter stop working. As, a result, (mucus and phlegm) associated with irritation (inflammation) forms; thereby decreasing the diameter of the airway (D2) and causing the passages to become clogged and restricted. The decreased diameter (D2) airway (A2) prevents the proper flow of air into and out of the lung inhibiting the natural functions of the lung.

Emphysema is defined as a breakdown or destruction in the walls of the alveoli causing them to become abnormally enlarged. A lung (10) affected by emphysema has enlarged and engorged alveoli (14). The breakdown or destruction of the alveoli (14) reduces the surface area available for the exchange of oxygen and carbon dioxide during breathing resulting in poor oxygenation (low oxygen and high carbon dioxide levels within the body). Also, elasticity of the lung (10) itself is decreased leading to the loss of support of the airway embedded in the lung (10) which often times leads to collapse of the airway thereby further limiting airflow.

FIGS. 3A and 3B are cross-sectional views of normal alveoli (14) and alveoli (14) affected by emphysema, respectively. FIG. 3A depicts and enlarged view of normal alveoli (14) showing the grape-like configurations or individual alveolus (20) and surrounding tissue (22). The individual alveolus (20) is tightly compacted together and is clearly defined by the surrounding tissue (22). However, with emphysema, as the alveoli (14) deteriorates or is destroyed, the surrounding tissue (22) loses its elasticity thereby causing the individual alveolus (20) to expand and become engorged, see FIG. 3B. FIG. 3B also shows that the individual alveolus (20) is much less compacted and has reduced amounts of surrounding tissue (22). Due to the inelasticity of the surrounding tissue (22), the abnormally enlarged alveoli (14) fill easily with air during inhalation/inspiration, but lose the ability to empty the lung during exhalation/expiration.

In both cases of COPD, chronic bronchitis and emphysema, the greatest reduction in airflow occurs when breathing out (exhalation/expiration) because the pressure in the chest tends to compress rather than expand the airways. A person with COPD may not be able to completely finish breathing out before needing to take another breath. A small amount of the air from the previous breath remains within the lungs when the next breath is started. Easy filling and poor emptying of the lungs leads to progressive hyperexpansion or dynamic hyperinflation of the lungs resulting in inefficient breathing mechanics. Hyperexpansion/hyperinflation of the lungs, in addition to the poor oxygenation capability, makes it progressively difficult to breathe.

In order to compensate for the breathing deficiencies, some people with advanced COPD manage to breathe faster; however, as a result, they usually develop dyspnea (chronic shortness of breath). Others, who may be less short of breath, tolerate the low oxygen and high carbon dioxide levels in their bodies, but eventually develop headaches, drowsiness and even heart failure. Advanced COPD can lead to complications beyond the lung such as depression, muscle loss, weight loss, pulmonary hypertension, osteoporosis and heart disease.

Currently, there is no cure available for chronic bronchitis; most treatment is focused on making the symptoms less severe and trying to prevent further damage. The most common types of treatment involve changes in lifestyle, medication and supplemental oxygen supply. Examples of medications are bronchodilators to open airways; corticosteroids to reduce inflammation, swelling and phlegm production; and expectorants to stop the cough that often accompanies chronic bronchitis.

Lung Volume Reduction Surgery; herein after (LVRS), is a treatment option for patients with severe emphysema. In LVRS, a physician removes approximately 20-35% of the damaged lungs or of the poorly functioning space occupying the lung tissue from each lung. By reducing the lung size, the remaining lung and surrounding muscles are able to work more efficiently, making breathing easier.

LVRS is typically performed by techniques such as thoracoscopy, sternotomy and thoracotomy. Thoracoscopy is a minimally invasive technique where three small (approximately 1 inch) incisions are made in each side, between the ribs. A video-assisted thoracic surgery (VATS) or videoscope is placed through one of the incisions which allows the surgeon to see the lungs. A special surgical stapler/grasper is inserted in the other incisions and is used to cut away the damaged areas of the lung, reseal the remaining lung from leaking blood and air, and dissolvable sutures are used to close the incisions. Thoracoscopy can be used to operate on either one or both lungs and allows for assessment and resection of any part of the lungs. Thorascopic laser treatment of portions of the lung can also be performed using this technique. In contrast, thorascopic laser treatment, although capable of ablating emphysematous tissue only at the lung surface, prohibits simultaneous bilateral lung applications.

Sternotomy or open chest surgery involves an incision being made through the breastbone to expose both lungs. Both lungs are reduced in this procedure, one after the other. The chest bone is wired together and the skin is closed. This is the most invasive technique and is used when thoracoscopy is not appropriate. This approach is usually used only for upper lobe disease of the lung.

Thoracotomy is a technique often used when the surgeon is unable to see the lung clearly through the thoracoscope or when dense adhesions (scar tissue) are found. A 5 to 12 inch long incision is made between the ribs; and the ribs are separated, but not broken, to expose the lungs. With this procedure only one lung is reduced and the muscle and skin are closed by sutures.

Although the goal of surgical therapy of COPD is to prolong life by relieving shortness in breath, preventing secondary complications, and enhancing quality of life by improving functional status, LVRS for COPD has higher surgical risks than heart surgery. Other risks associated with LVRS involve, but are not limited to: air leakage from the lung tissue at the suture line and into the chest cavity, pneumonia, bleeding, stroke, heart attack and death (resulting from worsening of any of the aforementioned complications). Because of the dangers associated with LVRS and despite advances in medical therapy, a significant number of patients with advanced COPD face a miserable existence and are at an extremely high risk for death. Over the years, a number of minimally invasive methods have been developed to address the concerns related to LVRS and to focus on the selective destruction of specific areas of undesirable tissue as an alternative to LVRS. Some of these methods include cryosurgery, non-selective chemical ablation, and ablation through radiofrequency or (RF), ultrasound, microwave, laser and thermal electric methods. However, these developments are associated, as well, with a fair amount of surgically related setbacks including complications such as large and difficult to manipulate operating mechanisms and the inability to control therapy to the affected area. This is due to the fact that ablation techniques used historically have been non-selective in that they mediate cell death with methods such as extreme heat or cold temperatures. The aforementioned methods of focal destruction of affected areas have been proven to non-selectively and adversely affect blood vessels, nerves, and connective structures adjacent to the ablation zone. Disruption of the nerves locally impedes the body's natural ability to sense and regulate homeostatic and repair processes at and surrounding the ablation region. Disruption of the blood vessels prevents removal of debris and detritus. This also prevents or impedes repair systems, prevents homing of immune system components, and generally prevents normal blood flow that could carry substances such as hormones to the area. Without the advantage of a steady introduction of new materials or natural substances to a damaged area, reconstruction of, the blood vessels and internal linings become retarded as redeployment of cellular materials is inefficient or even impossible. Therefore historical ablation treatments do not leave tissue in an optimal state for self-repair in regenerating the region.

Improvements in medical techniques have rekindled interest in the surgical treatment of COPD, wherein the effects highly resemble that of LVRS but without much of the associated risks and complications of conventional LVRS techniques. These recent developments offer an opportunity to advance the regenerative process following ablation treatments. Irreversible Electroporation or (IRE) is one such technique that is pioneering the surgical field with improved treatment of tissue ablation. IRE has the distinct advantage of non-thermally inducing cell necrosis without raising/lowering the temperature of the ablation zone, which avoids some of the adverse consequences associated with temperature changes of ablative techniques such as radiofrequency (RF) ablation, microwave ablation, or even cryo-ablation. IRE also offers the ability to have a focal and more localized treatment of an affected area. The ability to have a focal and more localized treatment is beneficial when treating the delicate intricacies of organs such as the lung.

IRE is a minimally invasive ablation technique in which permeabilization of the cell membrane is effected by application of micro-second, milli-second and even nano-second electric pulses to undesirable tissue to produce cell necrosis only in the targeted tissue, without destroying critical structures such as airways, ducts, blood vessels and nerves. More precisely, IRE treatment acts by creating defects in the cell membrane that are nanoscale in size and that lead to a disruption of homeostasis while sparing connective and scaffolding structure and tissue. Thus, destruction of undesirable tissue is accomplished in a controlled and localized region while surrounding healthy tissue, organs, etc. is spared. This is different from other thermal ablation modalities known for totally destroying the cells and other important surrounding organs and bodily structures.

BRIEF SUMMARY OF THE DISCLOSURE

The present invention relates to methods for treating tissue, more particularly to treating lung tissue, through utilization of Irreversible Electroporation (IRE) to non-thermally ablate diseased tissue and enhance lung functions in patients with Congestive Obstructive Pulmonary Disorder (COPD).

It is a purpose of this invention to successfully treat target regions of diseased lung tissue affected by chronic bronchitis and emphysema through IRE ablation. IRE involves the application of energy sources capable of generating a voltage configured to successfully ablate tissue through the utilization of electrode balloons, flexible devices, probes such as monopolar, bipolar, or multiple probes (i.e. combinations of monopolar or bipolar probes arranged in a variety of configurations, monopolar and bipolar probes used together, or a series of separate or mixed groups of monopolar or bipolar probes), electrode arrays, and other devices available in electro-medicine. IRE ablation devices are available in various combinations and configurations in order to accommodate the ablation of multiple shapes, sizes and intricate portions of the diseased tissue. Examples of IRE probes applicable to this invention are described in U.S. patent application Ser. Nos. 12/413,332 filed Mar. 27, 2009 and 61/051,832 filed May 15, 2008, both of which are incorporated herein.

The present invention involves the method of treating COPD using IRE through open surgical, percutaneous, laparoscopical, or endrotracheal procedures including the steps of obtaining access to the diseased area by positioning one or more energy delivery devices coupled to an IRE device within a target region of diseased tissue; applying IRE energy the target region to ablate the tissue; disconnecting the energy source from the IRE probe and withdrawing the probe. More specifically, the invention involves ablating diseased portions of lung tissue. Although the method of the present invention is directed towards treatment of a diseased lung, the method can also be used to treat other organs or areas of tissue to include, but not limited to areas of the digestive, skeletal, muscular, nervous, endocrine, circulatory, reproductive, lymphatic, urinary, or other soft tissue or organs; and more particularly, areas of the liver, prostate, kidney, pancreas, uterus and brain, among others.

BRIEF DESCRIPTION OF THE DRAWINGS

FIG. 3A is an enlarged cross-sectional view of normal alveoli.

FIG. 3B is an enlarged cross-sectional view of alveoli affected by emphysema.

FIG. 6A is a perspective view of the percutaneous procedure of performing IRE detailing the use of an IRE probe to ablate the diseased region of the lung.

DETAILED DESCRIPTION OF THE INVENTION

Figure 1:
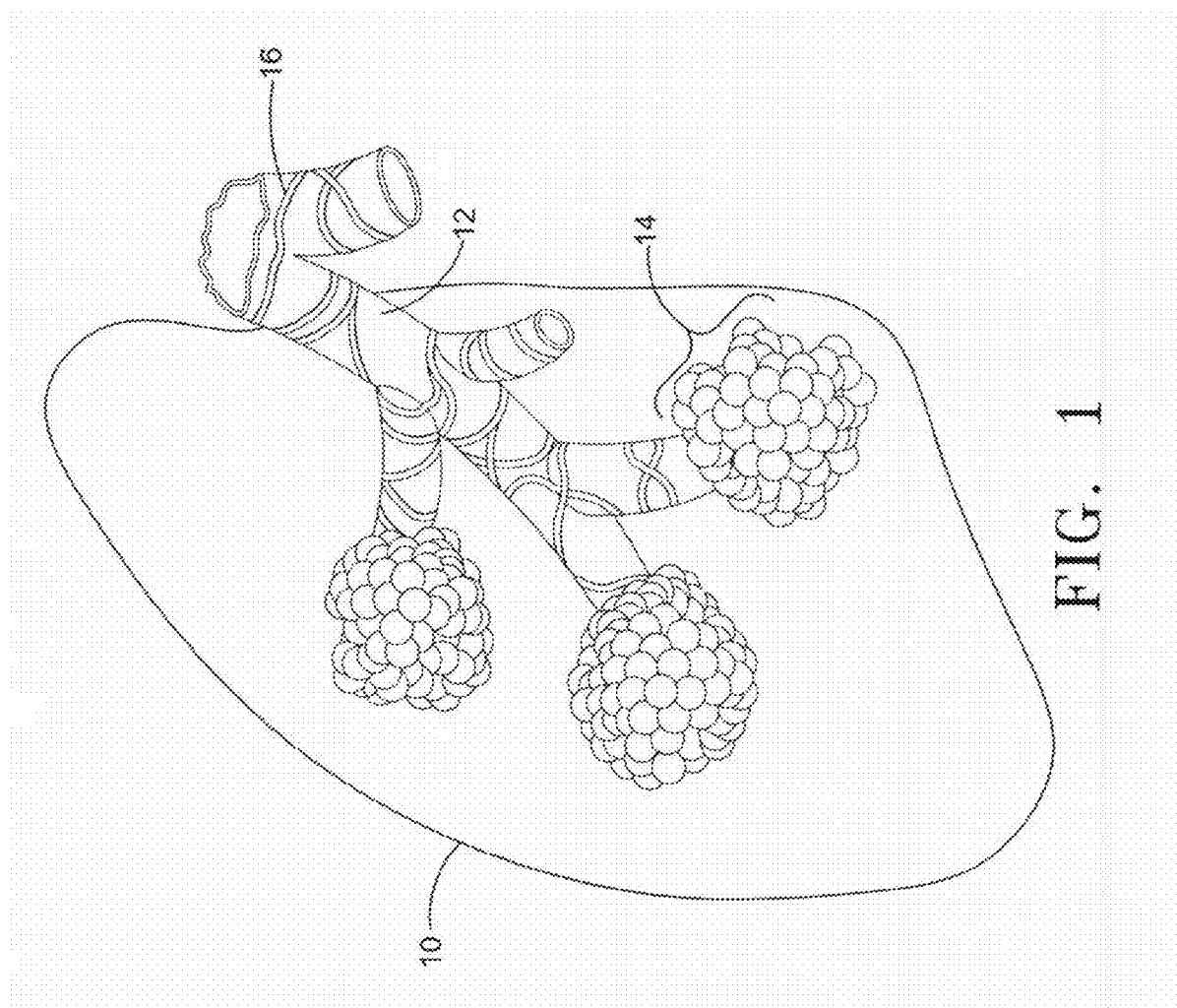
FIG. 1 is a perspective view of a lowermost portion of the lung depicting an enlarged bronchus and alveoli.
Figure 2A:
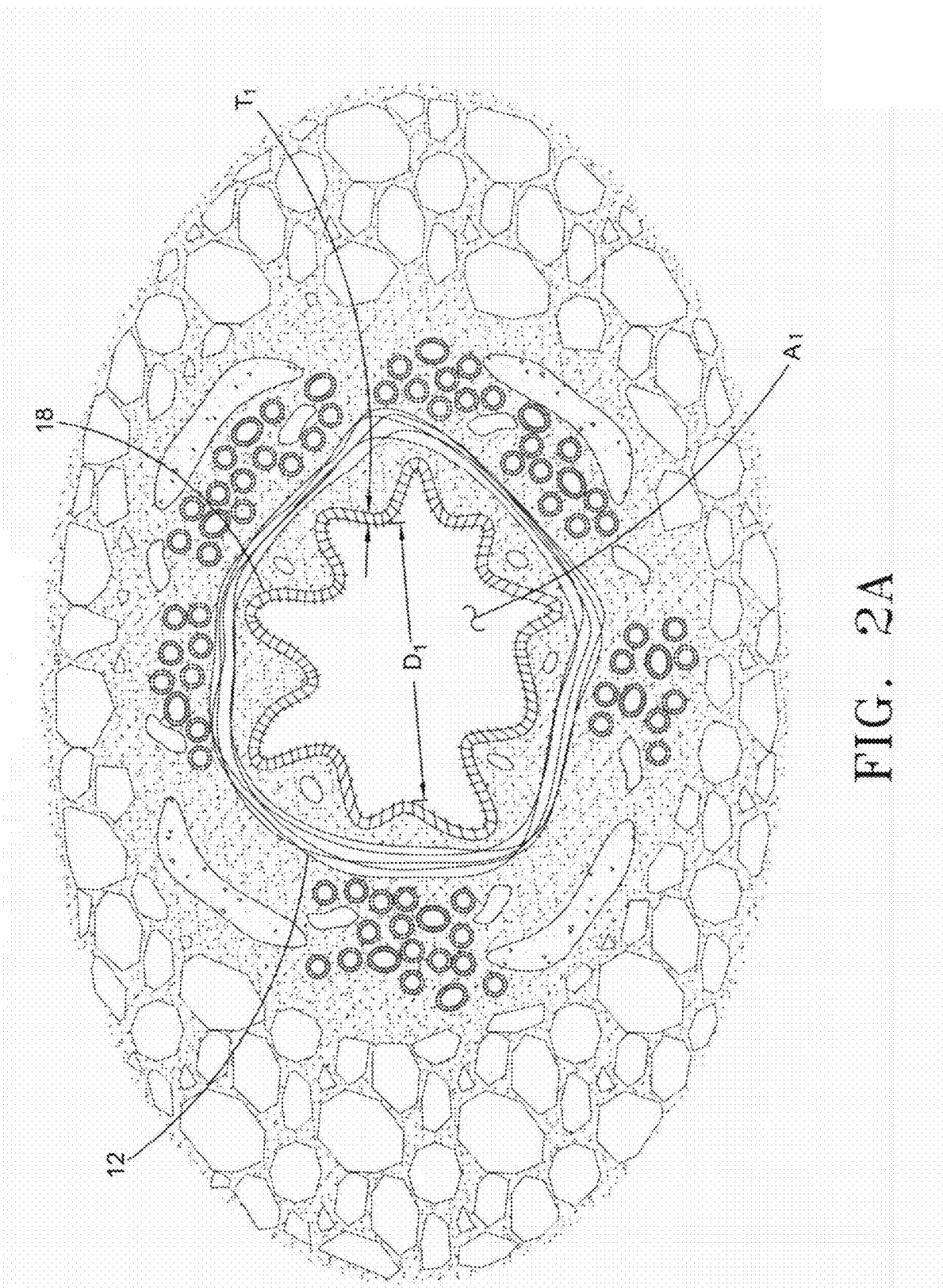
FIG. 2A is an enlarged cross-sectional view of a normal bronchus.
Figure 2B:
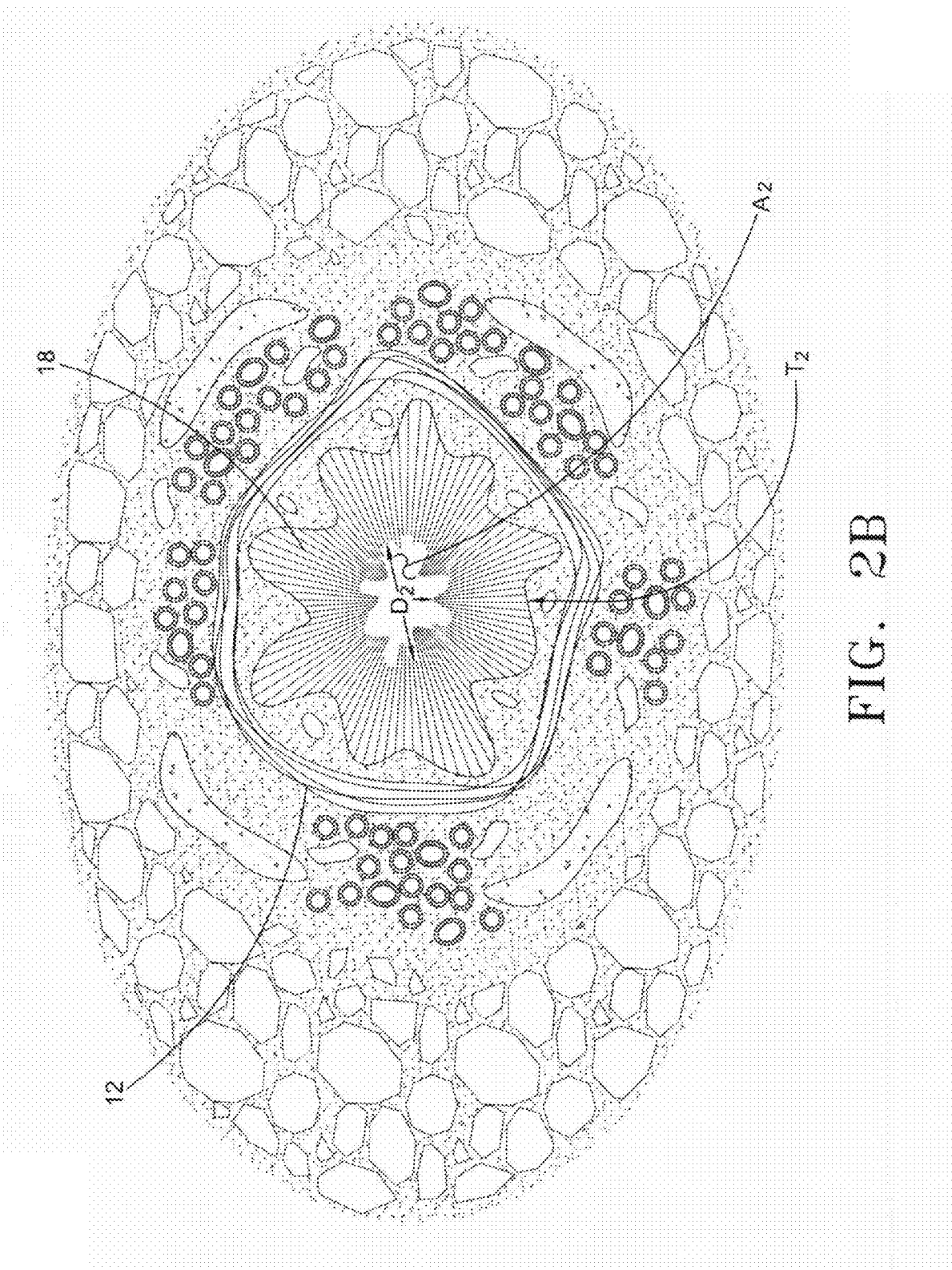
FIG. 2B is an enlarged cross-sectional view of a bronchus affected by chronic bronchitis.
Figure 4:
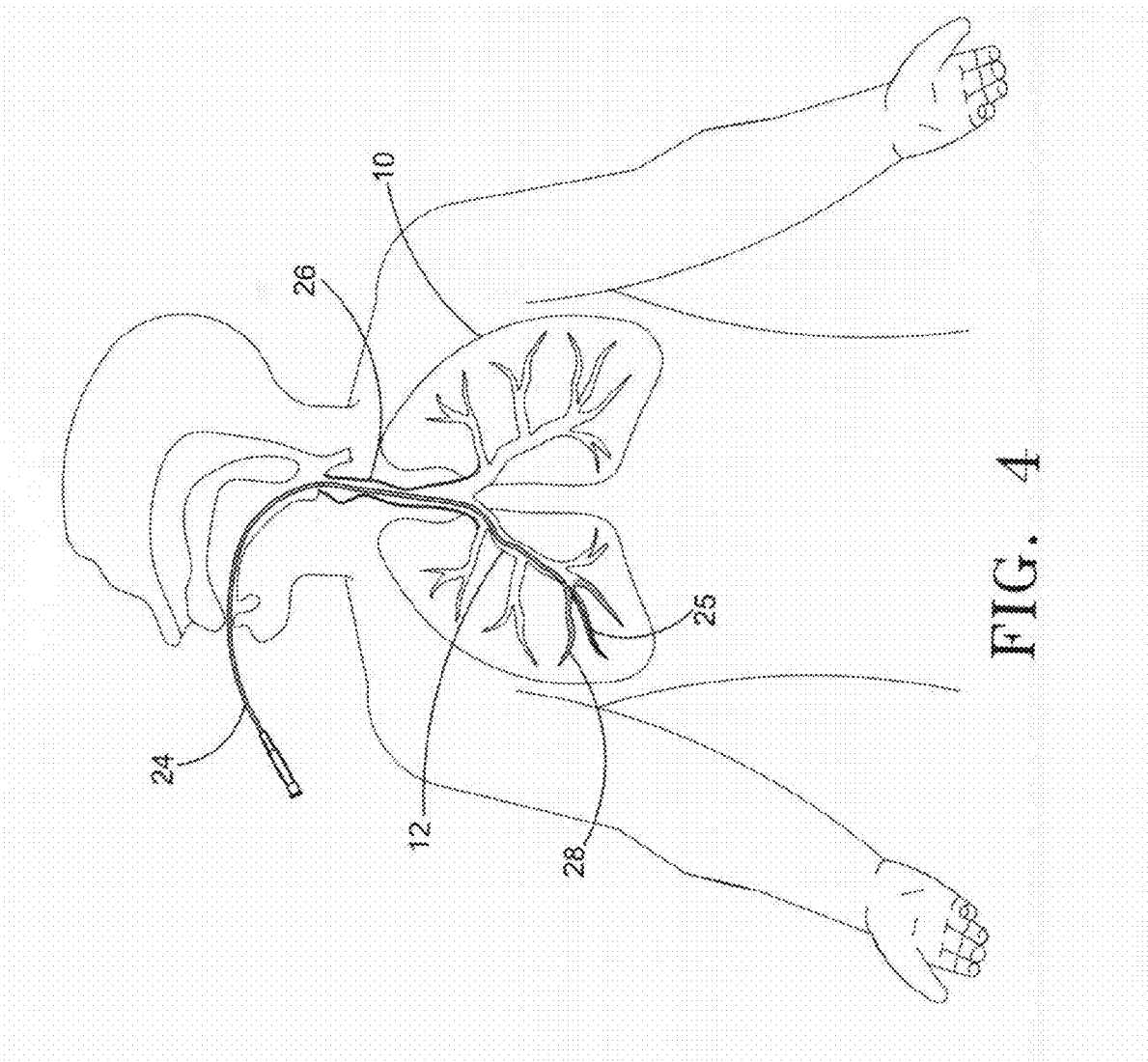
FIG. 4 is a perspective view of the endrotracheal procedure for performing IRE on a lung affected by chronic bronchitis showing a catheter passed through the trachea and positioned within the bronchus.

FIG. 4 shows the endrotracheal method of performing IRE on a lung (10) affected by chronic bronchitis. A catheter (24) is advanced through the trachea (26) to a diseased region (28) of the bronchus (12). Advancement through the trachea (26) is relatively simple and will optionally require a guidewire to select the advancement route through to the branching bronchus (12). Steering of the catheter (24) may be effected under real time imaging using video assisted thoracic surgery (VATS). Once the catheter (24) is in place inside the diseased region (28), a flexible IRE device (25) is inserted through the catheter (24) to the diseased region (28) of the bronchus (12). The flexible IRE device is used in the endrotracheal method because it allows for the device to be easily steered through and properly positioned within the delicate intricacies of the lung (10) and into the bronchus (12). With the flexible IRE device (25) within the diseased region (28) of the lung (10), an IRE power source (not shown) is powered on and IRE energy is applied to ablate the inflamed bronchial tissue of the diseased region (28). To treat multiple bronchi, the IRE device (25) may then be retracted back into the catheter (24) and redeployed in an adjacent bronchus (12).

Figure 5A:
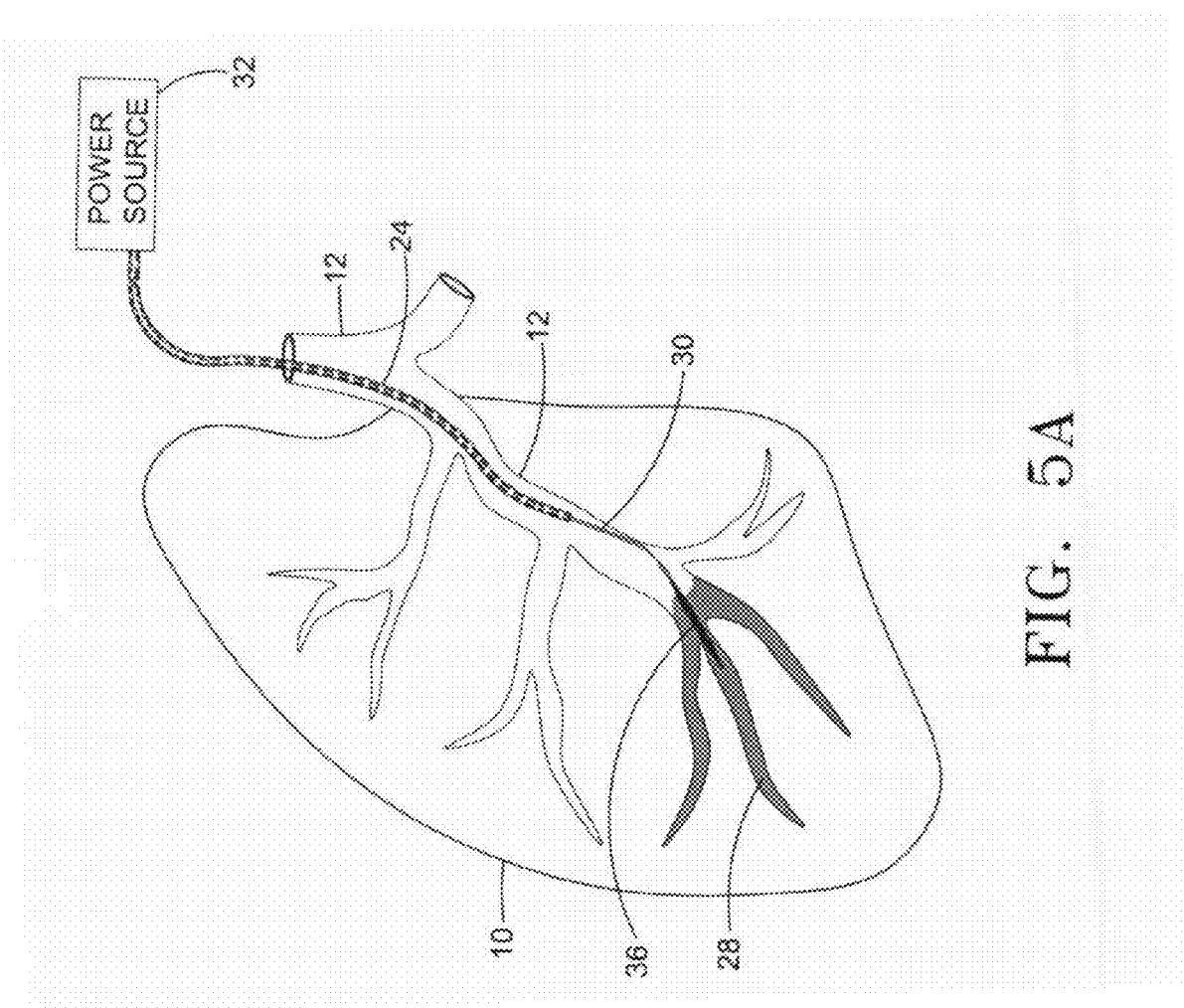
FIG. 5A is a perspective view of the endrotracheal procedure for performing IRE on a lung affected by chronic bronchitis showing an IRE electrode balloon positioned within the bronchus.
Figure 5B:
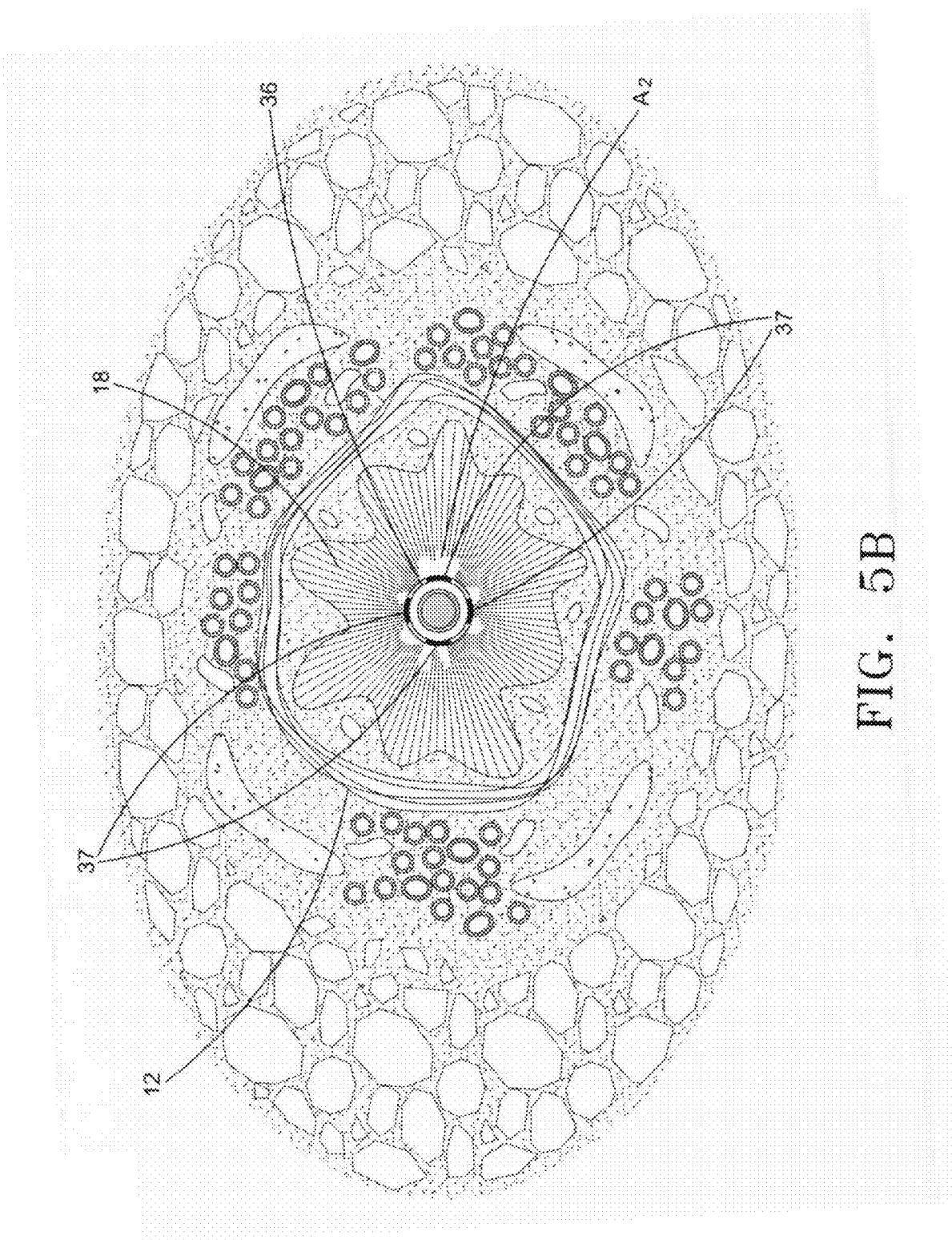
FIG. 5B is an enlarged cross-sectional view of a deflated IRE electrode balloon positioned within the bronchus prior application of IRE energy.
Figure 5C:
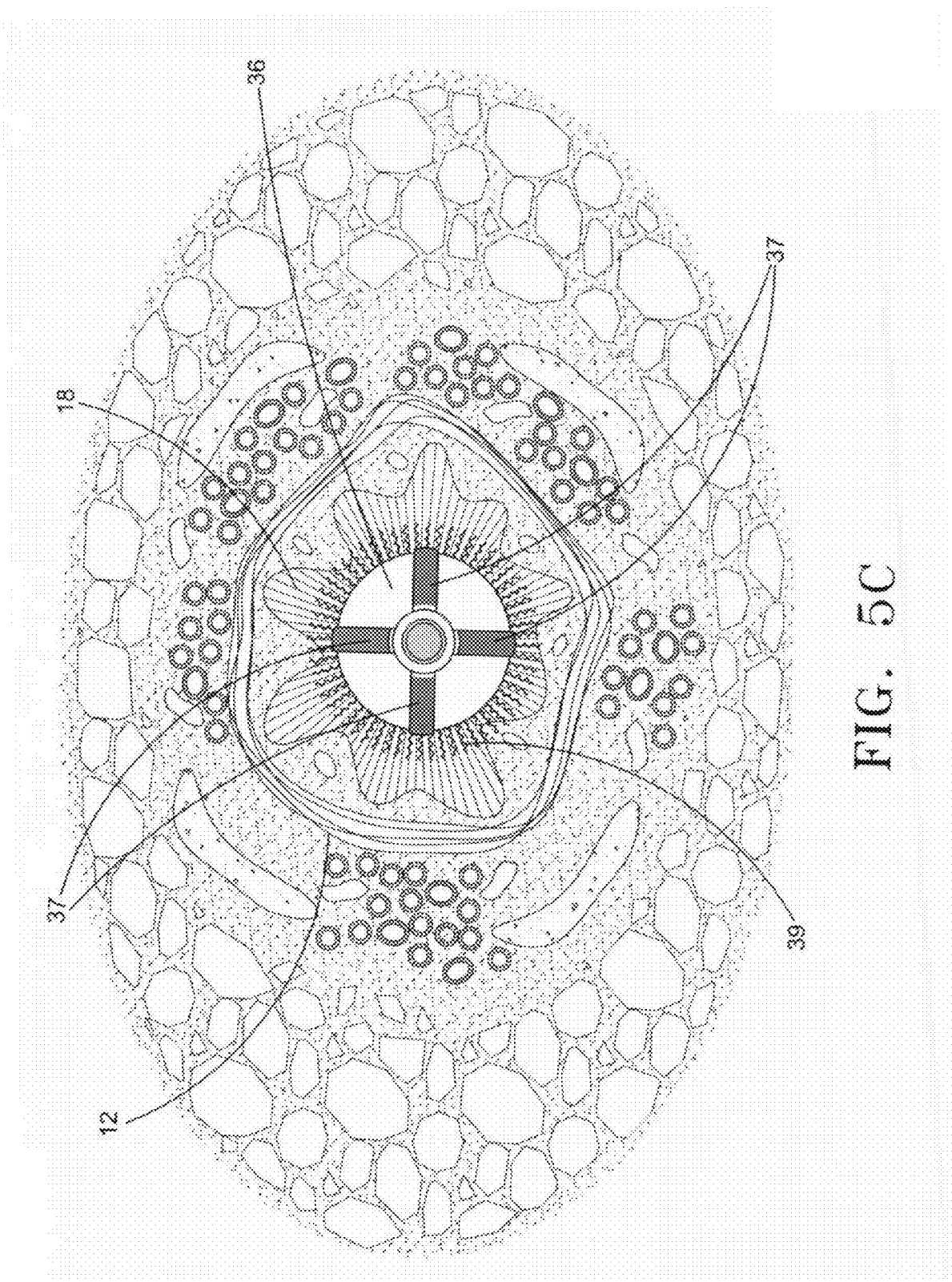
FIG. 5C is an enlarged cross-sectional view of an inflated IRE electrode balloon positioned within the bronchus during the application of IRE energy.
Figure 5D:
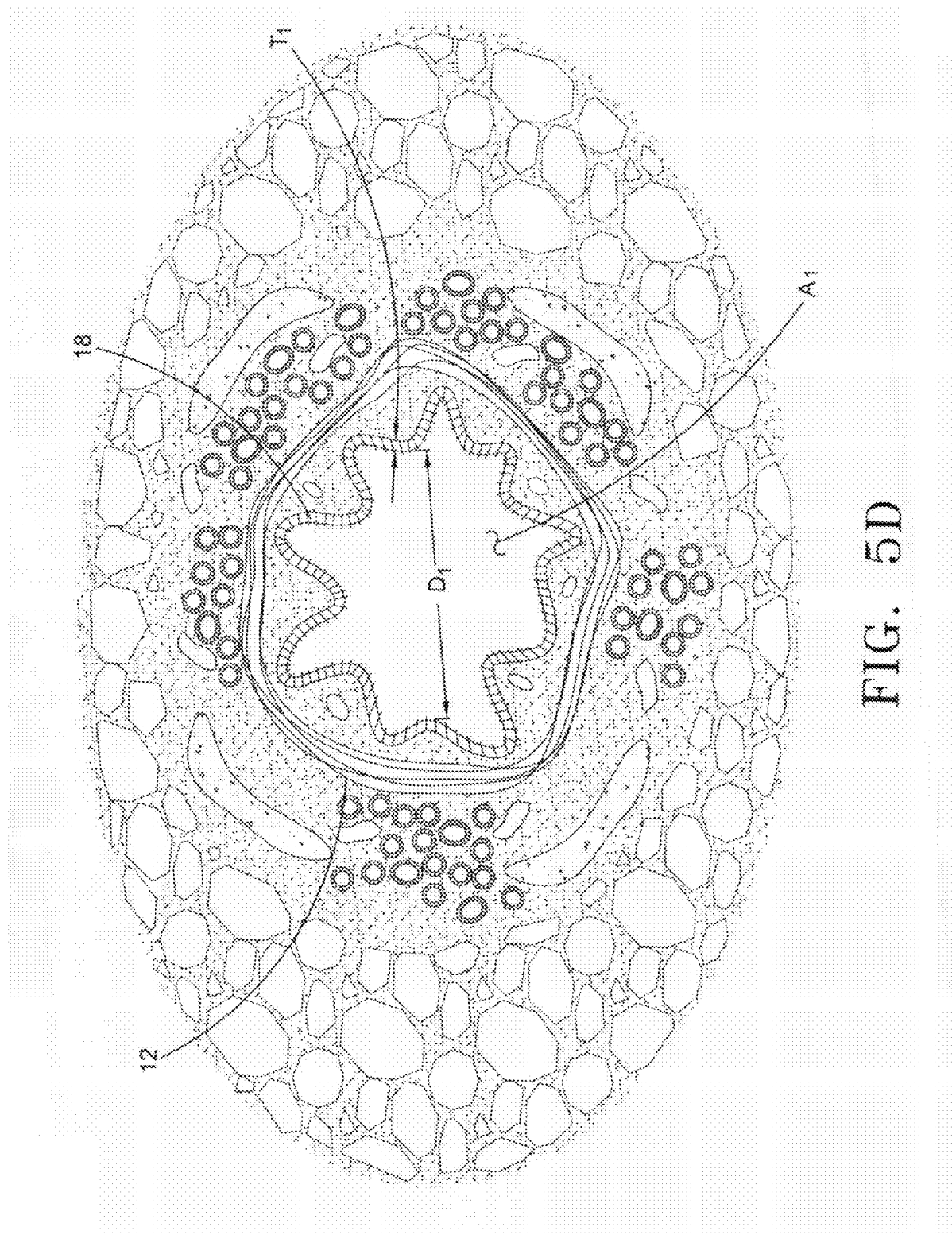
FIG. 5D is an enlarged cross-sectional view of the bronchus post-treatment showing the restored diameter of the bronchus.

The endrotracheal method of performing IRE can be executed endo-bronchially or exo-bronchially. FIG. 5A shows a more detailed view of the flexible IRE device (30) in place within the diseased region (28) of the lung (10) wherein the IRE device (30) includes an electrode balloon (36). Although an electrode balloon is shown, the endrotracheal procedure is not limited to such, other devices may be employed. FIG. 5B details the electrode balloon (36), in a deflated state, in place within the decreased diameter airway (A2) of the inflamed inner bronchial wall (18) of the bronchus (12). The electrode balloon (36) includes a plurality of electrodes 37 positioned on the surface of the deflated balloon. Prior to application of IRE energy, the IRE power source (32) is powered on, the electrode balloon (36) is inflated as shown in FIG. 5C. The expansion of the balloon results in a partial increase in bronchial airway diameter. Electrodes 37 are shown in contact with the inner bronchial wall (18) of the bronchus. As IRE energy is then applied to the inner bronchial wall (18) of the bronchus, electrical current (39) flows from the electrodes (37) into the bronchial wall (18) tissue. The inflamed portion of the bronchus is ablated, reducing the thickness of the bronchus wall. After treatment, the diameter (D1) of bronchial airway (A1) increases as shown in FIG. 5D. The airflow is restored and breathing functions improve.

A percutaneous method of treating a lung affected by chronic bronchitis may also be used. Very much similar to the endrotracheal method, the percutaneous method may be executed both endo-bronchially and exo-bronchially. The probe, with increased rigidity and strength relative to an IRE catheter probe, is inserted into the lung tissue through the skin using a direct stick approach. The distal end section of the probe is then advanced through a wall of the bronchus into the lumen. IRE energy is applied to ablate the tissue of the diseased region such that inflammation of the bronchus is decreased and breathing functions are enhanced.

Figure 6B:
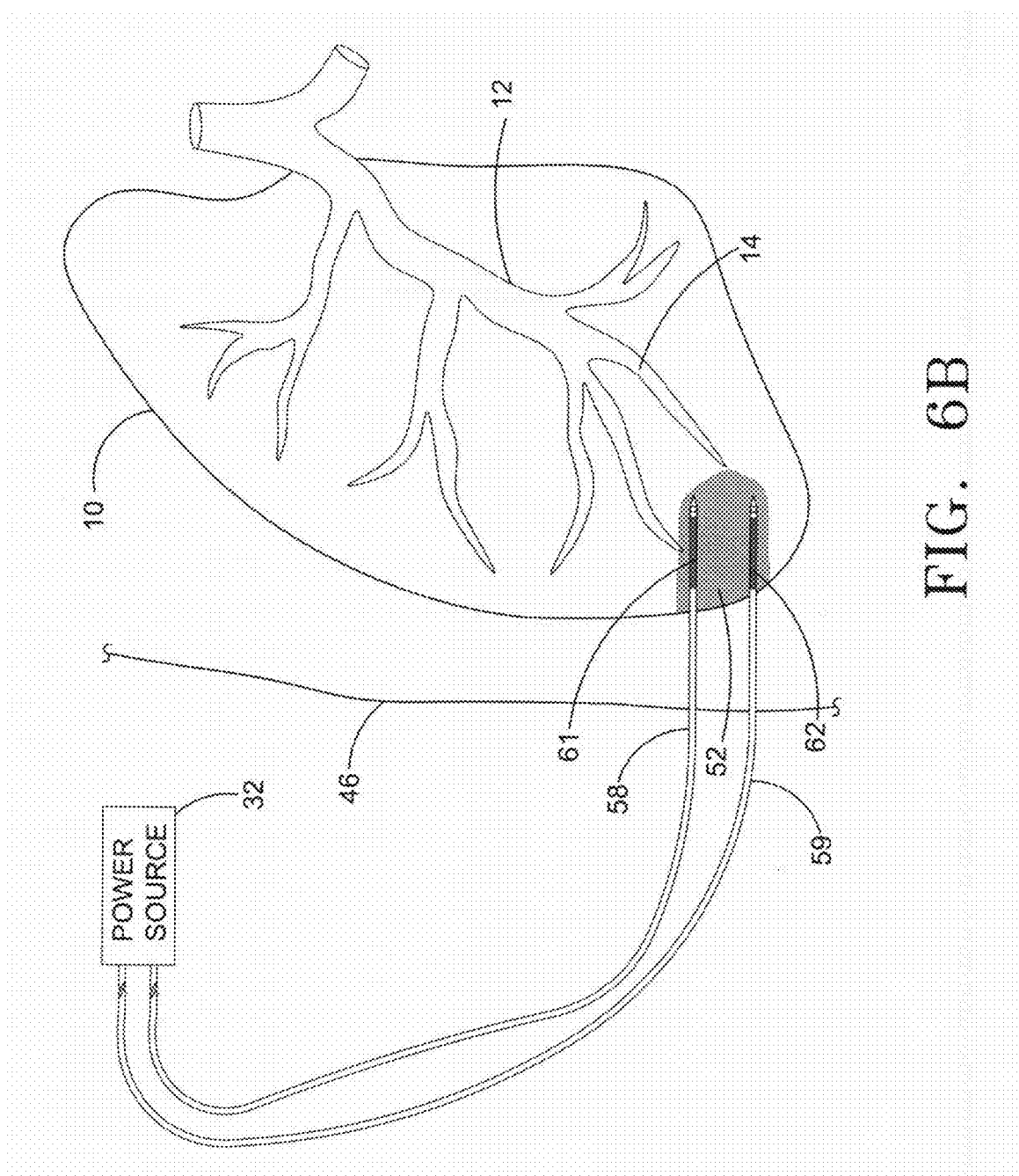
FIG. 6B is a perspective view of the percutaneous procedure of performing IRE detailing the use of two IRE probes to ablate the diseased region of the lung.

FIGS. 6A and 6B show a method of performing IRE on an emphysemic lung (10) using a percutaneous approach. Although not shown, the endrotracheal approach previously described may also be used. FIG. 6A details a bipolar IRE probe (50) inserted through the skin (46) to the target area of the lung (10) near the alveoli (14). Advancement and positioning of the probe (50) may be effected under real time imaging modalities such as ultrasound or CT. Once the probe (50) is in place in the targeted lung region, the IRE power source (32) is powered on and IRE energy is applied to the probe. Electrical current flows between distal electrode (56) and proximal electrode (54), creating a zone of ablation (52).

Alternatively, as shown in FIG. 6B, two IRE probes of opposite polarity may be used to ablate a desired lung tissue volume. Electrode probe (58), which may be of positive polarity, is positioned within the lung tissue a selected distance away from negative electrode probe (59). The application of electrical energy from power source (32) creates an electrical field between the two electrodes 61 and 62 as shown by ablation zone (52). In another embodiment (not shown), an electrode probe with deployable electrode tines may be used to apply IRE energy to lung tissue. In all these embodiments, the ablated tissue dies, thereby reducing the overall lung volume. For larger target areas, sequential ablations may be performed. As with LVRS, up to approximately 20-35% of the damaged lung may be non-surgically ablated. By reducing the lung volume, the remaining lung tissue and surrounding muscles are able to work more efficiently, improving air flow.

Ablation of the targeted region of diseased tissue is achieved with an IRE generator as the power source, utilizing a standard wall outlet of 110 volts (v) or 230v with a manually adjustable power supply depending on voltage. The generator should have a voltage range of 100v to 10,000v and be capable of being adjusted at 100v intervals. The applied ablation pulses are typically between 20 and 100 microseconds in length, and capable of being adjusted at 10 microsecond intervals. The preferred generator should also be programmable and capable of operating between 2 and 50 amps, with test ranges involving an even lower maximum where appropriate. It is further desired that the IRE generator includes 2 to 6 positive and negative connectors, though it is understood that the invention is not restricted to this number of connectors and may pertain to additional connector combinations and amounts understood in the art and necessary for optimal configurations for effective ablation. Preferably, IRE ablation involves 90 pulses with maximum field strengths of 400V/cm to 3000V/cm between electrodes. Pulses are applied in groups or pulse-trains where a group of 1 to 15 pulses are applied in succession followed by a gap of 0.5 to 10 seconds. Pulses can be delivered using probes, needles, and electrodes each of varying lengths suitable for use in not only with percutaneous and laparoscopic procedures, but with open surgical procedures as well. In endrotracheal procedures, due to the delicate intricacies and general make-up of the lung, it is preferable that a flexible device be used to ensure proper placement and reduced risk of perforation, abrasion, or other trauma to the lung tissue.

Although preferred specifics of IRE ablation devices are set forth above, electro-medicine provides for ablation processes that can be performed with a wide range of variations. For instance, some ablation scenarios can involve 8 pulses with maximum field strengths between electrodes of 250V/cm to 500V/cm, while others require generators having a voltage range of 100 kV-300 kV operating with nano-second pulses with maximum field strengths of 2,000V/cm to, and in excess of, 20,000V/cm between electrodes. Electrodes can be made using a variety of materials, sizes, and shapes known in the art, and may be spaced at an array of distances from one another. Conventionally, electrodes have parallel tines and are square, oval, rectangular, circular or irregular shaped; having a distance of 0.5 to 10 centimeters (cm) between two electrodes; and a surface area of 0.1 to 5 cm2.

Figure 7:
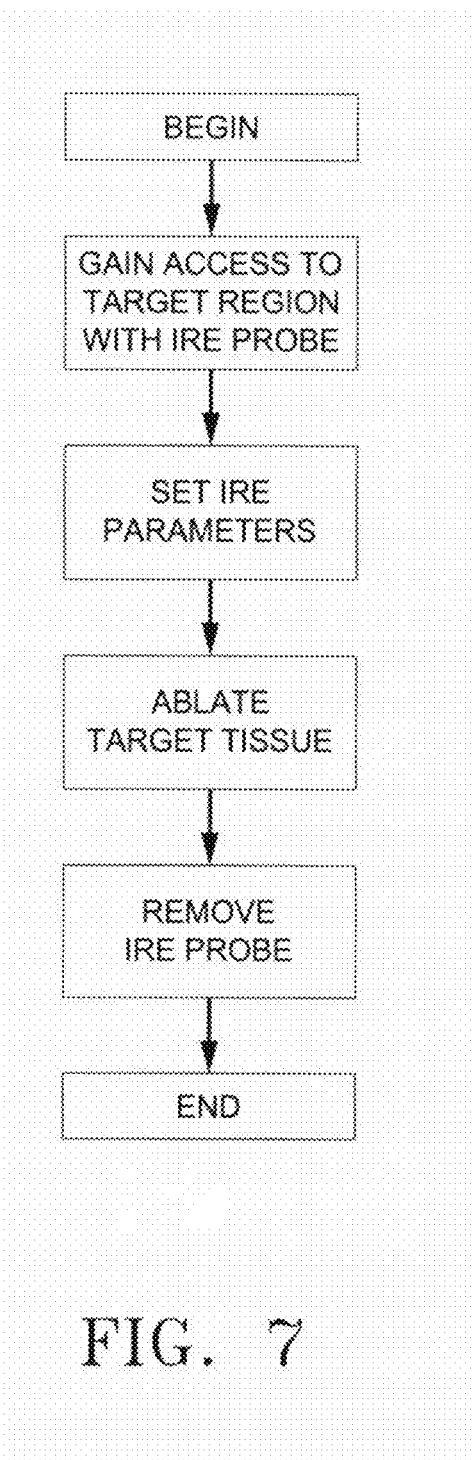
FIG. 7 is a flowchart showing the method of treating patients with COPD or chronic bronchitis using IRE ablation.

FIG. 7 is a flowchart detailing the basic method of performing IRE ablation on bronchitis or COPD patients. As detailed above, access to the diseased region is gained through open surgical, laparoscopical, percutaneous or endrotracheal procedure. Once the IRE device is connected and in proper position, the IRE parameters are set. These parameters may vary and are selected depending upon several factors such as the diseased state, patient health and anatomy, and other considerations. After establishing and setting the required IRE energy parameters, the diseased region of the lung is ablated and the IRE device is removed. Thus, focal tissue ablation of the lung is achieved without causing harm to surrounding tissue and/or organs.

An unlimited number of variations and configurations for the present invention could be realized. The foregoing discussion describes merely exemplary embodiments illustrating the principles of the present invention, the scope of which is recited in the following claims. Those skilled in the art will readily recognize from the description, the claims, and drawings that numerous changes and modifications can be made without departing from the spirit and scope of the invention. Accordingly, the scope of the invention is not limited to the foregoing specification.

What is claimed is:

1. A method of treating lung tissue comprising:
    obtaining access to the lung, wherein the lung comprises a target region and wherein the access comprises advancing at least one energy delivery device through the trachea, the at least one energy delivery device comprising an expandable member configured to expand at least one electrode;
    positioning the at least one energy delivery device within an airway of the target region, wherein the energy delivery device is coupled to an energy source;
    expanding the expandable member to partially expand the airway, and
    applying electrical pulses via the at least one electrode sufficient to irreversibly electroborate the target region.

2. The method of claim 1, wherein the step of positioning the at least one energy delivery device comprises: positioning the at least one energy delivery device within a diseased region of an inner wall of a bronchus of the lung.

3. The method of claim 2, wherein the step of inserting the at least one energy delivery device comprises; advancing the at least one energy delivery device through a patient's trachea prior to inserting the at least one energy delivery device within a diseased region of the bronchus.

4. The method of claim 3, wherein the step of applying the electrical pulses comprises applying the electrical pulses using a balloon electrode.

5. The method of claim 4, further comprising placing the balloon electrode in contact with the inner wall of the bronchus and ablating the target region to substantially increase a diameter of the bronchus.

6. The method of claim 2, wherein the step of positioning further comprises positioning the at least one energy delivery device endo-bronchially or exo-bronchially.

7. The method of claim 2, wherein the step of accessing further comprises positioning the at least one energy delivery device using one or more of a surgical, laparoscopic, percutaneous, and endotracheal method.

8. The method of claim 2, wherein the step of irreversible electroporation further comprises ablating a diseased region, wherein the diseased region is caused by bronchitis.

9. The method of claim 1, wherein the step of ablating further comprises ablating at an energy field strength in the range of between about 100V/cm to greater than about 10,000V/cm.

10. The method of claim 1, wherein the step of positioning the at least one energy delivery device comprises: inserting the at least one energy delivery device within a diseased region of an alveolus of the lung.

11. The method of claim 10, wherein the step of inserting the at least one energy delivery device comprises: obtaining access percutaneously prior to inserting the at least one energy delivery device within the target region of the alveolus.

12. The method of claim 11, wherein the step of applying the electrical pulses comprises applying the electrical pulses using a probe comprising deployable tines.

13. The method of claim 12, further comprising applying the electrical pulses directly into tissue adjacent the alveoli and ablating the target region to substantially decrease lung volume and increase lung function.

14. The method of claim 10, wherein the step of positioning further comprises positioning the at least one energy delivery device endo-bronchially or exo-bronchiaily.

15. The method of claim 14, wherein the method further comprises providing a catheter and inserting the flexible IRE device through the catheter to the target region.

16. The method of claim 15, wherein the method further comprises retracting the flexible IRE device into the catheter and redeploying the catheter into a bronchus of the lung.

17. The method of claim 1, wherein the step of irreversible electroporation further comprises applying the electrical pulses in a pulse train of between about 1 and about 15 electrical pulses.

18. The method of claim 10, wherein the step of irreversible electroporation further comprises ablating a diseased region, wherein the diseased region is caused by emphysema.

19. The method of claim 1, wherein the step of ablating further comprises delivering electrical pulses between 20 and 100 microseconds in length.

20. The method of claim 1. wherein the step of applying the electrical pulses comprises applying the electrical pulses using a flexible IRE device.

* * * * *